United States Patent
Howard

[11] Patent Number: 6,155,826
[45] Date of Patent: Dec. 5, 2000

[54] GRIP CHUCK SPINDLE ASSEMBLY FOR A DENTAL HANDPIECE

[76] Inventor: James Howard, 7192 Bestel Ave., Westminster, Calif. 92683

[21] Appl. No.: 09/426,008

[22] Filed: Oct. 25, 1999

[51] Int. Cl.[7] .................................................. A61C 1/14
[52] U.S. Cl. ..................................................... 433/129
[58] Field of Search .......................... 433/129, 127; 279/43, 50

[56] References Cited

U.S. PATENT DOCUMENTS

| | | | |
|---|---|---|---|
| 2,983,519 | 5/1961 | Staunt | 279/104 |
| 3,869,796 | 3/1975 | Thornburn | 32/26 |
| 4,015,335 | 4/1977 | Nash et al. | 32/27 |
| 4,089,115 | 5/1978 | Heil et al. | 32/27 |
| 4,370,132 | 1/1983 | Wohlgemuth | 433/128 |
| 4,436,512 | 3/1984 | Garcia | 433/129 |
| 4,493,645 | 1/1985 | Nakamishi | 433/127 |
| 4,536,157 | 8/1985 | Maizenberg | 433/19 |
| 4,575,338 | 3/1986 | Maizenberg | 433/126 |
| 4,595,363 | 6/1986 | Nakamishi | 433/129 |
| 4,752,444 | 6/1988 | Bowen et al. | 422/28 |
| 4,874,314 | 10/1989 | Fleer et al. | 433/129 |
| 5,040,980 | 8/1991 | Heil | 433/127 |
| 5,090,906 | 2/1992 | Penot | 433/127 |
| 5,165,896 | 11/1992 | Hein et al. | 433/129 |
| 5,542,846 | 8/1996 | Quinn et al. | 433/127 |
| 5,571,013 | 11/1996 | Novak | 433/127 |
| 5,704,786 | 1/1998 | Quinn | 433/128 |
| 5,718,582 | 2/1998 | Quinn et al. | 433/127 |
| 5,779,474 | 7/1998 | Gouser | 433/129 |

FOREIGN PATENT DOCUMENTS

| | | |
|---|---|---|
| 2509985 | 1/1983 | France . |
| 2555042 | 4/1985 | France . |
| 3402635 | 8/1985 | Germany . |
| 125303 | 6/1949 | Sweden . |

*Primary Examiner*—Todd E. Manahan
*Attorney, Agent, or Firm*—Dennis D. Beech

[57] ABSTRACT

The grip chuck spindle assembly is used to hold burs and drills in dental high speed handpieces. The grip chuck spindle assembly consists of three parts. An outer spindle which is hollow having three different diameter bores and a outer diameter sized to receive press fitted bearings and an impeller. A clamping bushing at the bur end of the spindle which has two bores one to freely accept burs and drills and a smaller bore at the end with longitudinal slots that run into a tear drop hole which together form the two clamping fingers. The third part is a plunger with one wedge shape end which engages the clamping bushing slots, and when pressure is applied to the plunger the wedge spreads the end of the clamping bushing open to allow removal or insertion of a bur or drill. The entire assembly is held together by the bur end, i.e., the larger bore end, of the spindle being crimped closed.

5 Claims, 2 Drawing Sheets

GRIP CHUCK SPINDLE ASSEMBLY FOR A DENTAL HANDPIECE

BACKGROUND OF THE INVENTION

1. Field of the Invention

The present invention relates to spring grip chucks and more particularly, to button releasing spindle chucks used in dental high speed handpieces for holding dental burs and drills.

2. Description of Related Art

There are currently known a wide variety of devices for insertion and removal of dental burs and drills in the head end of dental handpieces. These apparatus use push buttons or pressure piston, actuation levers, wedge shape plungers and other actuation means to disengage a clamping mechanism retaining a dental bur or drill in a dental handpiece to allow removal and insertion. The grip chuck spindles are retained in the rotational elements, bearings and impeller, of the head end of a dental handpiece.

U.S. Pat. No. 5,040,980 discloses a dental handpiece having a chuck with spring jaws that exert a griping force on a dental bur or drill. The jaws are opened to release the bur or drill by a lever at the upper end of the handpiece head. When the lever is moved upward, a wedge plunger is propelled between the jaws to spread them apart and release or insert a bur or drill. This and other lever actuated chucks have not been as widely used as the button actuated chuck spindles due to two major disadvantages. First, the movement of the lever is difficult and a tear in the doctors protective latex gloves is not uncommon. The second and larger problem is that the lever exerts double the pressure downward on the spindle chuck assembly which in turn is transmitted through the bearings supporting the spindle chuck resulting in premature bearing problems. Significant effort is being made to successfully convert these lever type chucks and caps to the preferred button actuating chucks and caps.

U.S. Pat. No. 4,874,314 discloses a dental handpiece having a socket which includes a sleeve that accepts a clamping sleeve which has two longitudinal slots extending inward to form resilient tongues which are moveable from a clamping position for engaging the bur or drill. The socket includes an axially movable ram which is actuated by a handle for the purpose of moving the tongues from the clamping position to an unclamped position to allow releasing of a tool. However the disadvantage of this design is in the ram and clamping sleeve where the ram has an outside tapered conical surface for engaging one end of the clamping sleeve which is provided with an inwardly tapered surface. To achieve the tapered conical surface on the ram, material thickness is minimal and is easily deformed when in use. If the ram tapered conical area is deformed during use the opening of the clamping sleeve does not occur and is unable to accept or release a tool. The other disadvantage is that the ram conical surfaces which are weaker than the clamping sleeve tongues, are to be used to spread the clamping sleeve tongues apart. If the ram tapered conical area flexes inward during use the bur or drill can not be accepted by the ram resulting in a failure to accurately position the bur or drill.

West German Patent No. DE 3402635 disclose a dental handpiece having a chuck with spring jaws that exert a griping force on a dental bur or drill. The jaws are shifted into bur/drill releasing or insertion position by depressing of a push button at the upper end of the handpiece head. When the button is depressed, a wedge plunger is propelled between the jaws to spread them apart and release or insert a bur/drill. However, field experiences with such a completed construction reveal operational problems that until the present invention have defied simple effective solution.

The present invention is structured to solve the currently available and disclosed devices assembly and operational problems for which there has been a long felt need in the dental industry. The grip chuck spindle assembly is designed for simple, easy assembly and for relatively smaller forces to install and remove burs and drills. The device is comprised of three parts, an outer spindle, a clamping bushing and a plunger, all of which are secured by crimping the bur end of the spindle against the clamping bushing bur end. The invention in the preferred embodiment is assembled by first inserting the plunger in the spindle followed by the clamping bushing with clamping fingers oriented toward the inserted plunger. The unit is operated by pushing the plunger to cause the wedge end to force the clamping fingers apart to allow insertion and removal of dental burs and drills. The simple operational approach and structure results in improved operational concentricity of rotational elements, reliability and less cost of manufacture.

SUMMARY OF THE INVENTION

One object of the present invention is to provide an improved spindle grip chuck assembly for use in dental high speed handpieces that has a higher reliability and performance. A further object of the present invention is to provide such a device which is of simple, inexpensive construction. Another object that results form the simple design is that a higher concentricity between the spindle chuck assembly and dental bur or drill can be achieved.

In accordance with the description presented herein, other objectives of this invention will become apparent when the description and drawings are reviewed.

DESCRIPTION OF THE PREFERRED EMBODIMENT

Figure 1:
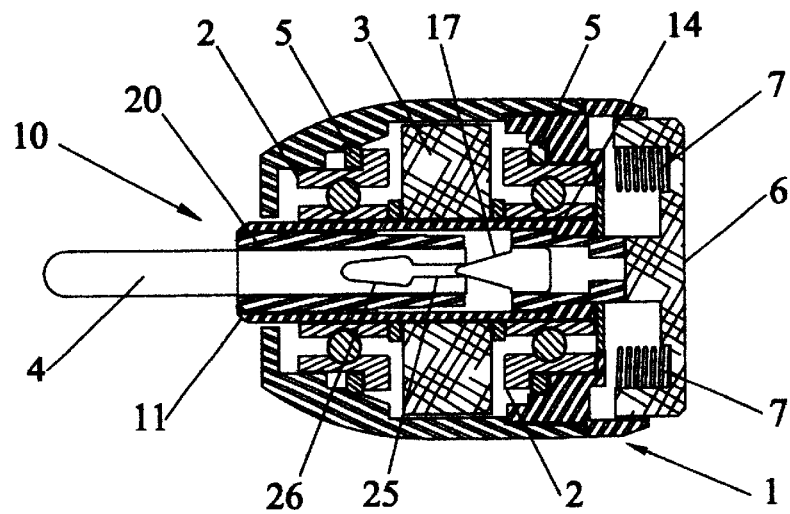
FIG. 1 illustrates a cross section perspective view of the head end portion of a dental handpiece embodying the grip chuck system of the present invention.
Figure 2:
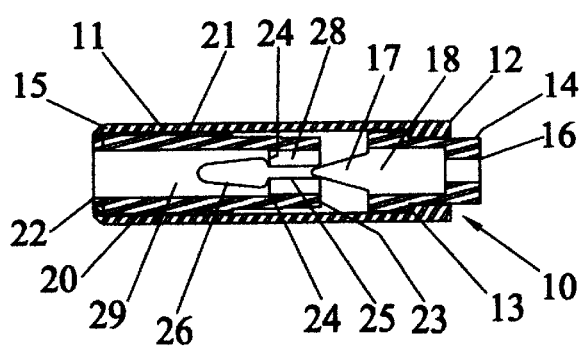
FIG. 2 illustrates a cross section view of the spindle grip chuck assembly according to the present invention.
Figure 3:
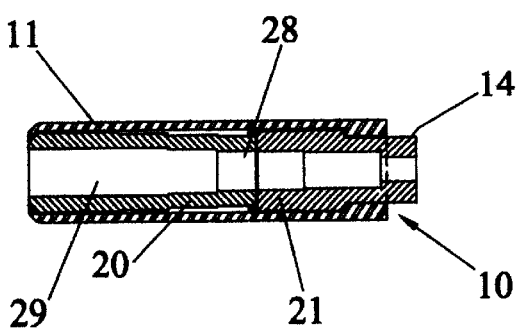
FIG. 3 illustrates a cross section view at a 90 degree perspective to FIG. 1 of the spindle grip chuck assembly.
Figure 4:
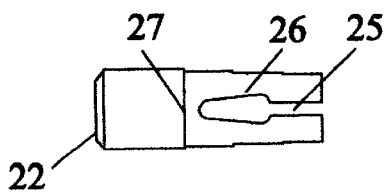
FIG. 4 illustrates the clamping bushing separate from the spindle grip chuck assembly.
Figure 4A:
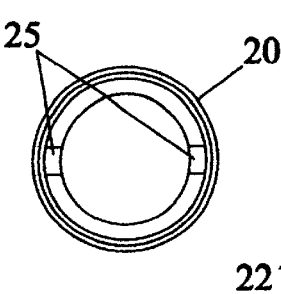
FIG. 4A. is a top end view of the clamping bushing.
Figure 5:
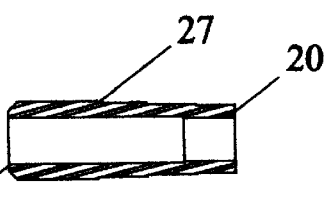
FIG. 5 illustrates a cross section of the clamping bushing rotated 90 degrees from FIG. 4 perspective.
Figure 6:
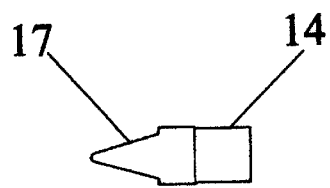
FIG. 6 illustrates the plunger shown separate from the spindle grip chuck assembly.
Figure 7:
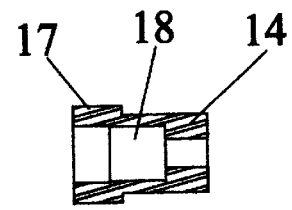
FIG. 7 illustrates a cross section of the plunger rotated 90 degrees from FIG. 6 perspective.
Figure 8:
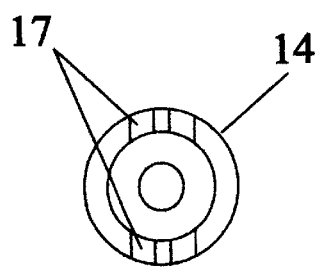
FIG. 8 illustrates a wedge end view of the plunger.

The grip chuck spindle assembly has a spindle with an outer diameter sized to have bearings and an impeller of a dental handpiece press fit thereon for rotational operation in the head end of the dental handpiece. The spindle, which is generally of hollow cylindrical shape, has a plunger slidably inserted therein with the plunger wedge end oriented to engage slots of a clamping bushing which is also inserted in the spindle. The plunger and clamping bushing are retained in the spindle by crimping the bur end of the spindle against the bur end, which is slightly beveled, of the clamping bushing. Dental burs and drills are retained in the assembly by clamping fingers which may be disengaged by movement of the plunger against the slots. This allows removal and insertion of dental burs and drills.

Referring to FIGS. 1 through 10, a dental handpiece head end (1) as commonly understood in the art for rotational action to power a dental bur (4), drill or other tool has bearings (2) and impeller (3) press fit on spindle (11). The bearings (2) are usually mounted in the head end (1) with O-rings (5) as interface elements. For the preferred embodiment a push button (6) with bias springs (7) is used to engage the grip chuck spindle assembly (10).

Figure 9:
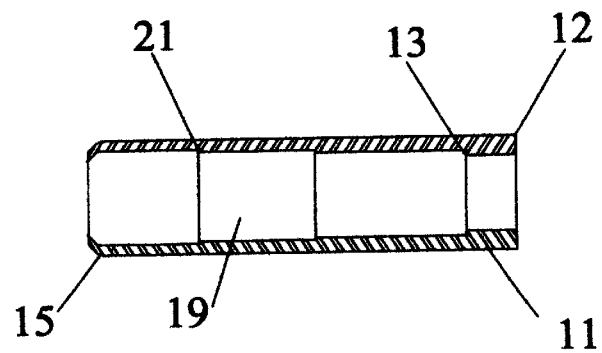
FIG. 9 illustrates a longitudinal cross section view of the spindle with four diameter bores.
Figure 10:
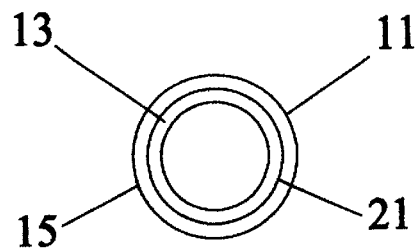
FIG. 10 illustrates a bur end view of the spindle.

The spindle (11) is generally the shape of an open ended hollow cylinder. The interior is formed to create three different diameter bores with the plunger end (12) of smallest diameter to create step (13) to retain the plunger (14) and intermediate the plunger end (12) and bur end (15) an intermediate diameter bore exists to create bushing step (21) to retain clamping bushing (20). In FIG. 9 a fourth diameter bore (19) is best seen as increasing a portion of the internal diameter between bushing step (21) and the step (13) of the spindle (11). This bore may be used as a means to provide additional clearance for the spreading of the clamping end (23) of the clamping bushing.

The plunger (14) is cylindrical shaped and sized to be slidably inserted in the spindle (11) from the bur end (15) such that the button end (16) protrudes through the plunger end (12). The wedge end (17) is thereby oriented to engage the clamping bushing (20). There is a plunger bore (18) for receipt of a dental bur (4).

The clamping bushing (20) is of generally an open ended hollow shape cylinder with a bore (29) and having a bur end (22) and clamping end (23). Two clamping fingers (24) are formed at the clamping end (23) by slots (25) ending in oval apertures (26). When the clamping bushing is slidably inserted in the spindle (11) it engages the plunger (14) by means of the slots (25). The clamping bushing (20) is retained in the spindle (11) by annular seat (27) contact with bushing step (21) and by crimping of spindle bur end (15) against clamping bushing bur end (22), which is beveled, or by roll forming or other like means of the bur end (15).

A dental bur (4) or drill is retained in the grip chuck spindle assembly (10) by the clamping action of the clamping fingers (24) which have a reduced diameter clamping bore (28) at the clamping end (23) and the spring force of the clamping fingers (24) spread by the presence of a dental bur (4). The spring force exists and is characterized by the shape of the slots (25) and oval apertures (26) as well as the material of the clamping bushing (20). This form factor is desirable as a progressive course of material tension is established in the clamping fingers (24) which is reliable in retaining a dental bur (4) or drill yet does not require excessive force, as with lever action assemblies, to disengage the clamping action.

In the case of the preferred embodiment the simple action of a user's finger on the push button (6) causes the plunger (14) to slide longitudinally in the spindle (11) such that the wedge end (17) forces the clamping fingers (24) to spread apart and release the dental bur (4). It has been found through experiment that a clamping bushing (20) formed of high strength stainless steel hardened to 52 Rockwell C Scale provides the best performance for operation of the assembly. Good results have been achieved using a grade known as 420 F.

While the invention has been particularly shown and described with respect to the illustrated and preferred embodiments thereof, it will be understood by those skilled in the art that the foregoing and other changes in form and details may be made therein without departing from the spirit and scope of the invention.

I claim:

1. A grip chuck spindle assembly for dental handpieces comprising:

a spindle of generally open ended hollow cylindrical shape with outside diameter to be mounted in a dental handpiece and having at least three different diameter bores therein;

a plunger end of the spindle having the smallest diameter bore therein for retention of a plunger slidably inserted in the spindle wherein the plunger seats against a step such that a button end protrudes from the spindle;

a spindle bur end having the largest diameter bore therein and thereby creating in the spindle an intermediate diameter bore therein for retention of a clamping bushing of generally open ended cylindrical hollow shape having a bore formed therein, the clamping bushing slidably inserted in the spindle wherein the clamping bushing having an annular seat which seats against a bushing step and the spindle bur end is pressed against the clamping bushing bur end;

a clamping end of the clamping bushing having a plurality of clamping fingers formed by a plurality of slots each with an oval aperture formed therein and a portion of the clamping end having a clamping bore therein which is of smaller diameter than the clamping bushing bore; and the plunger having a wedge end which engages the slots such that when a force is exerted to press the plunger along the longitudinal axis the wedge end spreads the clamping fingers apart for disengaging a dental tool retained therein.

2. The grip chuck spindle assembly as in claim 1 wherein the plunger having a plunger bore formed therein for receiving a dental tool shaft.

3. The grip chuck spindle assembly as in claim 2 wherein there is a smaller diameter bore relative to the plunger bore formed in the button end.

4. The grip chuck spindle assembly as in claim 1 wherein the spindle having a fourth diameter bore element intermediate the step and the bushing step.

5. The grip chuck spindle assembly as in claim 1 wherein the clamping bushing is formed of high strength stainless steel hardened to 52 Rockwell C Scale.

* * * * *